(12) United States Patent
Meyer et al.

(10) Patent No.: US 7,711,424 B2
(45) Date of Patent: May 4, 2010

(54) SELECTION OF CARDIAC SIGNAL FEATURES DETECTED IN MULTIPLE CLASSIFICATION INTERVALS FOR CARDIAC PACING RESPONSE CLASSIFICATION

(75) Inventors: Scott A. Meyer, Rochester, MN (US);
Yanting Dong, Shoreview, MN (US);
Kevin John Stalsberg, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 247 days.

(21) Appl. No.: 12/070,004

(22) Filed: Feb. 14, 2008

(65) Prior Publication Data

US 2008/0140145 A1 Jun. 12, 2008

Related U.S. Application Data

(63) Continuation of application No. 11/116,525, filed on Apr. 28, 2005, now Pat. No. 7,337,000.

(51) Int. Cl.
*A61N 1/362* (2006.01)
*A61N 1/365* (2006.01)
(52) U.S. Cl. .............................. 607/27; 607/28; 600/510
(58) Field of Classification Search .................. 607/27, 607/28; 600/510
See application file for complete search history.

(56) References Cited

U.S. PATENT DOCUMENTS

| | | | |
|---|---|---|---|
| 5,431,693 A | 7/1995 | Schroeppel | |
| 5,443,485 A | 8/1995 | Housworth et al. | |
| 5,683,431 A | 11/1997 | Wang | |
| 6,128,535 A | 10/2000 | Maarse | |
| 6,148,234 A | 11/2000 | Struble | |
| 6,221,011 B1 | 4/2001 | Bardy | |
| 6,270,457 B1 | 8/2001 | Bardy | |
| 6,277,072 B1 | 8/2001 | Bardy | |
| 6,280,380 B1 | 8/2001 | Bardy | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,398,728 B1 | 6/2002 | Bardy | |
| 6,440,066 B1 | 8/2002 | Bardy | |
| 6,449,503 B1 * | 9/2002 | Hsu ........................... | 600/518 |
| 6,512,953 B2 | 1/2003 | Florio et al. | |
| 6,915,164 B2 | 7/2005 | Bradley et al. | |
| 6,963,775 B2 | 11/2005 | Russie et al. | |
| 7,062,327 B2 | 6/2006 | Bradley et al. | |
| 2003/0208241 A1 | 11/2003 | Bradley et al. | |

(Continued)

OTHER PUBLICATIONS

U.S. Appl. No. 11/116,525, filed Apr. 28, 2005, Meyer et al.

(Continued)

*Primary Examiner*—Carl H. Layno
*Assistant Examiner*—Tammie K Heller
(74) *Attorney, Agent, or Firm*—Hollingsworth & Funk, LLC

(57) ABSTRACT

Cardiac devices and methods involve the detection of cardiac signals features in adjacent classification intervals. Portions of the cardiac signal features detected in adjacent classification intervals are associated and are used to classify the cardiac response to a pacing pulse. Associating the portions of the cardiac signal features may be based on expected signal morphology.

20 Claims, 11 Drawing Sheets

U.S. PATENT DOCUMENTS

| | | |
|---|---|---|
| 2005/0131476 A1 | 6/2005 | Kim et al. |
| 2005/0131477 A1 | 6/2005 | Meyer et al. |
| 2006/0074454 A1 | 4/2006 | Freeberg |
| 2006/0129193 A1 | 6/2006 | Zhang |
| 2006/0129194 A1 | 6/2006 | Zhang |
| 2006/0129195 A1 | 6/2006 | Sathaye et al. |
| 2006/0129196 A1 | 6/2006 | Dong et al. |
| 2006/0129197 A1 | 6/2006 | Zhang et al. |
| 2006/0129198 A1 | 6/2006 | Zhang et al. |
| 2006/0129199 A1 | 6/2006 | Zhang et al. |

OTHER PUBLICATIONS

U.S. Appl. No. 11/116,544, filed Apr. 28, 2005, Meyer et al.
U.S. Appl. No. 11/116,558, filed Apr. 28, 2005, Dong et al.
U.S. Appl. No. 11/116,565, filed Apr. 28, 2005, Stalsberg et al.
U.S. Appl. No. 11/116,578, filed Apr. 28, 2005, Stalsberg et al.

* cited by examiner

SELECTION OF CARDIAC SIGNAL FEATURES DETECTED IN MULTIPLE CLASSIFICATION INTERVALS FOR CARDIAC PACING RESPONSE CLASSIFICATION

RELATED APPLICATIONS

This application is a continuation of U.S. patent application Ser. No. 11/116,525, filed on Apr. 28, 2005, now U.S. Pat. No. 7,337,000 which is hereby incorporated herein by reference.

FIELD OF THE INVENTION

The present invention relates generally to implantable medical devices and, more particularly, to cardiac devices and methods directed to cardiac pacing response classification.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically include circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Detecting if a pacing pulse "captures" the heart and produces a contraction allows the cardiac rhythm management system to adjust the energy level of pace pulses to correspond to the optimum energy expenditure that reliably produces capture. Further, capture detection allows the cardiac rhythm management system to initiate a back-up pulse at a higher energy level whenever a pace pulse does not produce a contraction.

When a pace pulse produces a contraction in the heart tissue, the electrical cardiac signal preceding the contraction is denoted the captured response (CR). The captured response typically includes an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example. The evoked response may be affected by interaction with intrinsic heart activity and resulting in a fusion or pseudofusion response.

A fusion beat is a cardiac contraction that occurs when two cardiac depolarizations of a particular chamber, but from separate initiation sites, merge. At times, a depolarization initiated by a pacing pulse may merge with an intrinsic beat, producing a fusion beat. Fusion beats, as seen on electrocardiographic recordings, exhibit various morphologies. The merging depolarizations of a fusion beat do not contribute evenly to the total depolarization of the myocardium.

Pseudofusion occurs when a pacing stimulus is delivered on a spontaneous P wave during atrial pacing or on a spontaneous QRS complex during ventricular pacing. In pseudofusion, the pacing stimulus may be ineffective because the tissue around the electrode has already spontaneously depolarized and is in its refractory period.

Methods and systems of the present invention are directed to processes for effectively determining capture and may be used to discriminate between various types of pacing responses, including, for example, capture, fusion/pseudofusion, and noncapture.

SUMMARY OF THE INVENTION

The present invention is directed to cardiac pacing response classification based on detected features of a cardiac signal following a pacing pulse.

One embodiment of the invention involves a method for classifying a cardiac response to pacing. The method includes sensing a cardiac signal in adjacent classification intervals following delivery of a pacing pulse. One or more features of the cardiac signal are detected in a boundary region of the adjacent classification intervals. The cardiac response to the pacing pulse is based on the one or more cardiac signal features detected in the boundary region.

According to one aspect of the invention, the cardiac signal may be evaluated across the adjacent classification intervals to determine feature information associated with the cardiac signal features. Portions of the cardiac signal features detected in adjacent classification intervals may be associated based on expected signal morphology, e.g., an expected time variation associated with the cardiac signal features. The cardiac pacing response classification is performed based on the associated portions of the one or more cardiac signal features.

Another embodiment of the invention is directed to a system for characterizing a cardiac response to pacing. The system includes sensing circuitry configured to sense cardiac signals following pacing pulses delivered to a heart. The system further includes a processor coupled to the sensing circuitry. The processor is configured to provide adjacent classification intervals and to detect one or more features of the cardiac signals in a boundary region of the adjacent classification intervals. The processor is configured to classify the cardiac response to the pacing pulse based on the one or more cardiac signal features detected in the boundary region.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
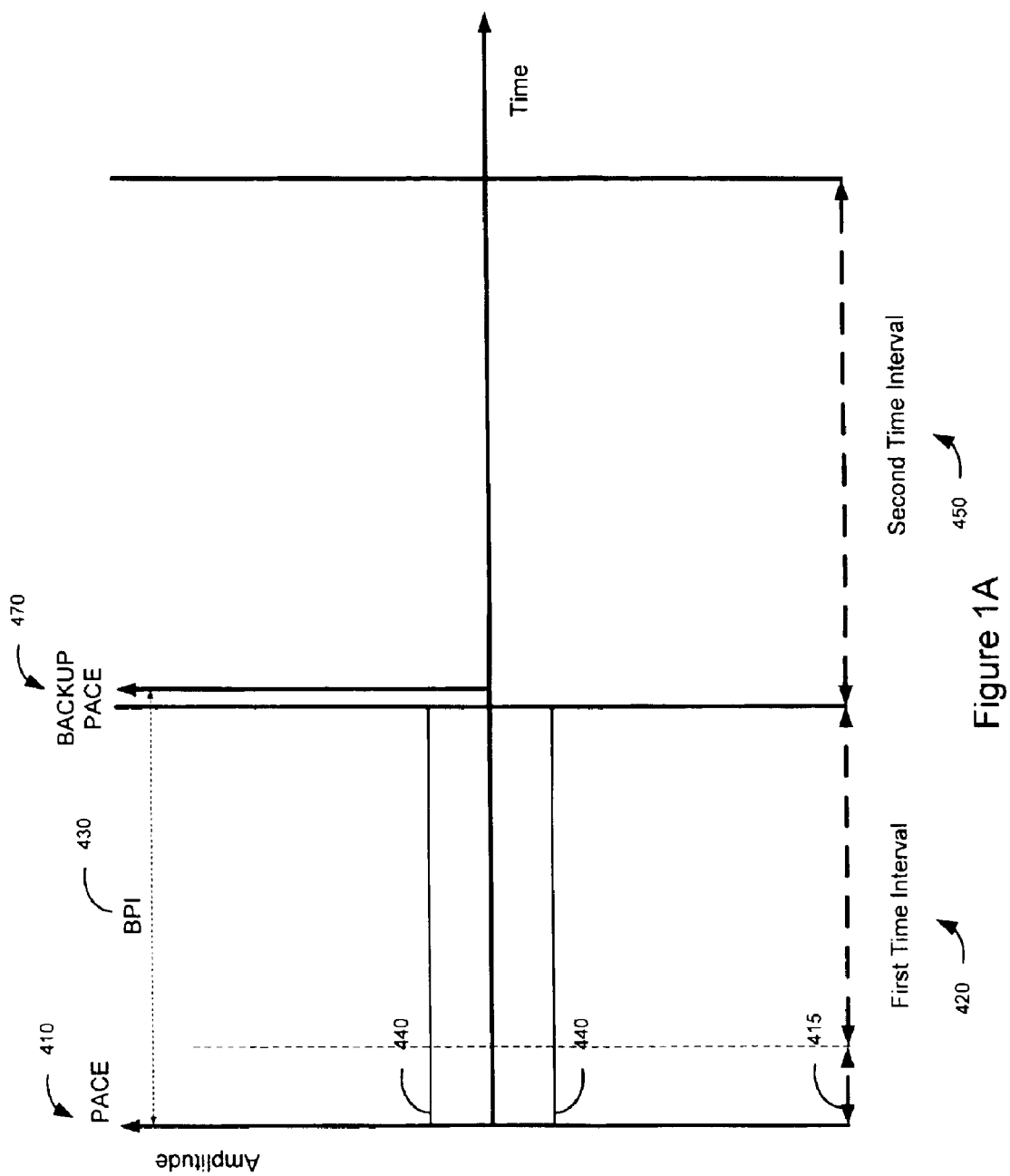
FIG. 1A illustrates one example of classification intervals that may be implemented for cardiac response classification in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Cardiac pacing response classification may be implemented by a pacemaker or other cardiac rhythm management (CRM) device. For example, cardiac pacing response classification may be utilized by the CRM device during automatic capture verification and/or capture threshold testing. The methods described herein use features of a cardiac signal following a pacing pulse to discriminate between various cardiac responses to the pacing pulse. Cardiac responses to pacing may include, for example, noncapture, capture, fusion/pseudofusion, and noncapture with intrinsic activity.

In some implementations, pacing response classification may involve sensing cardiac signals associated with pacing pulses in one or more classification intervals before and/or after the pacing pulse. FIG. 1A illustrates one example of classification intervals that may be implemented for cardiac response classification in accordance with embodiments of the invention. A pacing stimulation 410 is delivered to the heart, for example, to the right ventricle. The cardiac signal is blanked for a period of time 415, for example, about 0 milliseconds to about 40 milliseconds, following the delivery of the pacing stimulation 410. After the blanking period 415, a first time interval 420 is initiated. The duration of the first time interval 420 may be a programmable duration, for example, less than about 325 milliseconds. The cardiac signal associated with the pacing pulse is sensed during the first time interval 420. If the magnitude of the cardiac signal (either positive or negative) remains within a threshold range 440 in the first time interval 420, then the cardiac response may be classified as a noncaptured response. If noncapture is detected, then a backup pace 470 may be delivered following a backup interval (BPI) 430.

If the magnitude of the cardiac signal is beyond the threshold range 440, then various features of the cardiac signal may be detected and used for cardiac response discrimination. In some cases, sensing of the cardiac signal may be extended to additional time intervals, such as the second time interval 450. The second time interval 450 may be programmable, and may have a duration less than about 325 milliseconds. The durations of the additional time intervals may be different from, or the same as, the duration of the first time interval 420. A delay period may be established between the end of one time interval and the beginning of another time interval. The duration of the delay may be in a range of about 0 milliseconds (no delay) to about 40 milliseconds, for example.

The cardiac response to the pacing stimulation 410 may be classified based on characteristics of the cardiac signal sensed in the first 420 and/or the additional time intervals 450. Cardiac signal features are sensed in the first 420 and/or the additional time intervals 450. Classification of the cardiac pacing response may be based on the detected features and the classification interval in which the features are detected. If the features of the cardiac signal are sensed near the boundaries of the first 420 and/or the additional time intervals 450, an arbitration process may be performed in accordance with the present invention to more accurately determine the feature information.

Detection and classification of the captured response cardiac signal can be accomplished by extracting features of the cardiac signal that identify a capture response from fusion, pseudofusion, or noncapture responses. Where features are extracted across multiple adjacent classification intervals, it is possible for features near the boundary, yet on opposite sides of the boundary, to be associated. A correct classification can only be achieved by recognizing these associations and managing these boundary features so as to provide correct representation of the cardiac signal. The present invention involves various cardiac devices and methods that detect one or more features of cardiac signals in adjacent classification intervals, determine associations between features, near and on opposite sides of the boundary, and classify the cardiac response to a pacing pulse based on the features and their associations.

Use of arbitration processes in accordance with embodiments of the invention relaxes the requirement that a cardiac signal feature should be detected within a particular classification interval for pacing response discrimination. The first classification interval may be used as a boundary for detection of noncapture and to trigger delivery of a backup pace. However, features of the cardiac signal may transcend the boundary of the first classification interval into the second classification interval and still be used for pacing response classification. Thus, the first classification interval boundary may be used as a "hard" boundary for detection of noncapture and backup pacing, but as a "soft" or porous boundary for detection of cardiac signal features that may be used for pacing response discrimination. The embodiments of the present invention described herein may be used to allow fixed classification intervals to be successfully applied to a broader range of cardiac signal morphologies for pacing response classification.

Devices and methods in accordance with embodiments of the present invention detect one or more features of a cardiac signal across boundaries of adjacent classification intervals. The signal features are used to classify the cardiac response to the pacing pulse. As an example, consider the case where peak amplitude and peak timing of a captured response signal are consistent features that may be used to discriminate between the various cardiac pacing responses. The CRM may sense for peaks of the cardiac signal following the pacing pulse in first and second classification intervals as described above. If the peaks of the cardiac signal meet capture criteria, such as peak amplitude and/or peak timing criteria, then the cardiac pacing response may be classified as capture.

Figure 1B:
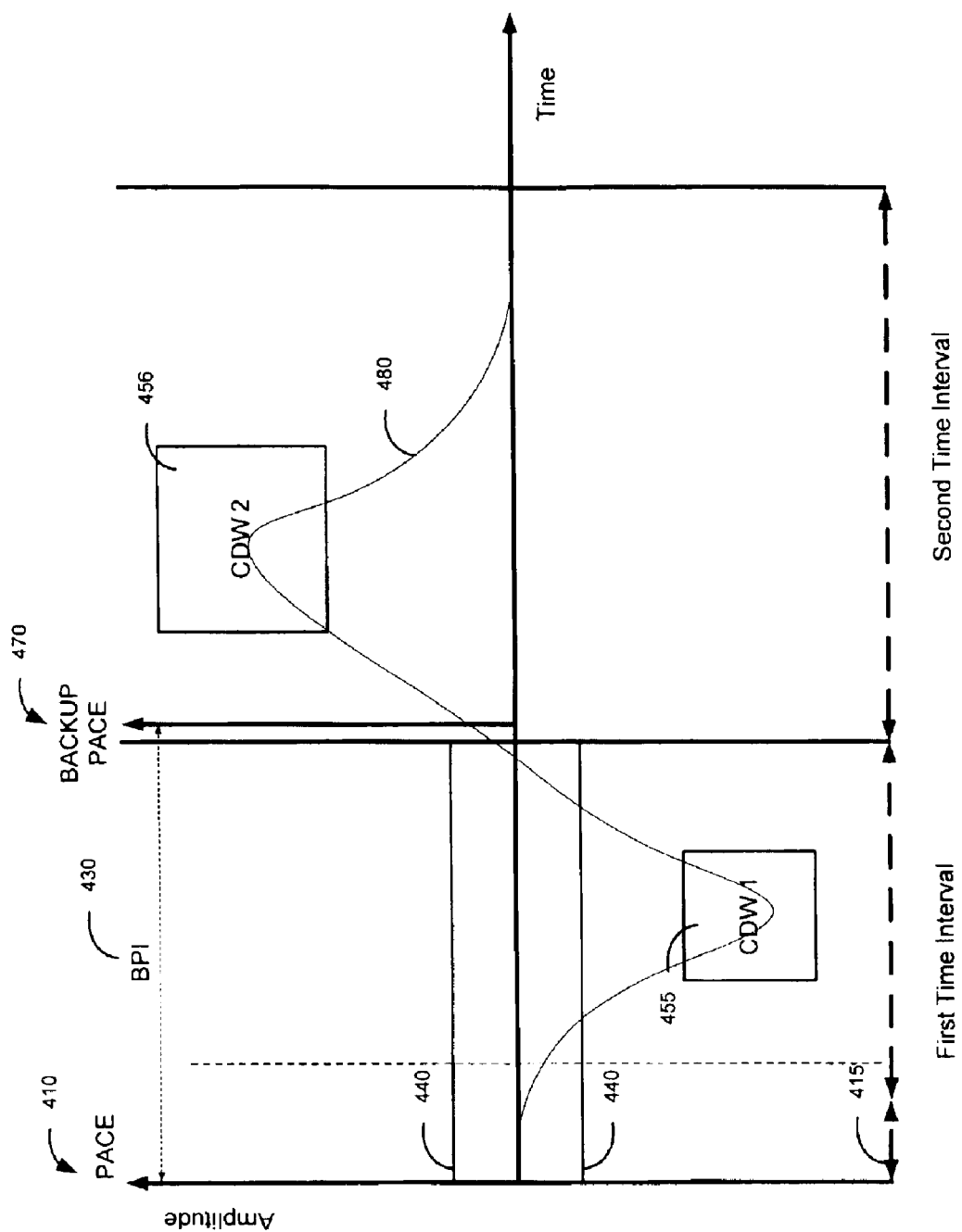
FIG. 1B illustrates a method of cardiac response classification based on detected cardiac signal peaks in accordance with embodiments of the invention.

FIG. 1B illustrates a method of cardiac pacing response classification based on detected cardiac signal peaks in accordance with embodiments of the invention. Following delivery of a pace 410, the sensing system is blanked, e.g., the sense electrodes are disconnected from sense amplifiers or the sense amplifiers are rendered inoperative, during a blanking period 415. Following the blanking period, the cardiac signal is sensed in one or more classification time intervals, 420 and 450 for example. In some scenarios, the second 450 and subsequent intervals (not shown) may be triggered by events occurring in one or more previous intervals.

In various implementations, sensing may be performed using the same electrode combination that was used to deliver the pacing stimulation. In other implementations, the pacing stimulation may be delivered using a first electrode configuration and sensing may use a second electrode configuration. Systems and methods for classifying a cardiac response to pacing using multiple time intervals and various sensing and pacing vectors are described in commonly owned U.S. patent application Ser. No. 10/733,869, filed Dec. 11, 2003, entitled "Cardiac Response Classification Using Multiple Classification Windows"; Ser. No. 10/734,599 filed Dec. 12, 2003, entitled "Cardiac Response Classification Using Retriggerable Classification Windows"; and Ser. No. 10/735,519 filed Dec. 12, 2003, entitled "Cardiac Response Classification Using Multisite Sensing And Pacing"; which are hereby incorporated herein by reference.

During the first classification time interval 420, the system senses for a cardiac signal magnitude (either positive or negative) beyond a positive or negative threshold range 440. If the positive or negative magnitude of the cardiac signal does not exceed the threshold 440 during the first classification time interval 420, then the cardiac response is classified as noncapture and a backup pace 470 may be delivered. The backup pace 470 is typically a high energy pace that is delivered following a backup interval (BPI) 430. For example, the BPI 430 may include an interval of about 100 ms timed from the delivery of the primary pace 410.

In one implementation involving capture detection and/or discrimination between capture and fusion beats, the system may utilize one or more capture detection windows 455, 456 as illustrated in FIG. 1B. The capture detection windows 455, 456 are areas defined in terms of amplitude and time in one or more classification time intervals 420, 450 following the pacing pulse. For example, the system may classify a cardiac response as capture if a peak value of the cardiac signal is detected in the first capture detection window 455 and a peak value of the cardiac signal is detected in the second capture detection window 456, as illustrated by the cardiac signal 480. Otherwise the cardiac response may be classified as a fusion/pseudofusion beat, or further discriminated. Additional detection windows may be defined for discriminating other types of cardiac responses such as noncapture with intrinsic activation, for example.

The parameters (timing and amplitude ranges) of the capture detection windows 455, 456 may vary based on the estimated or known cardiac signal morphology of the patient. Methods and systems involving the formation of templates representative of various types of cardiac pacing responses using detection windows are described in commonly owned U.S. patent application Ser. No. 11/116,544, filed Apr. 28, 2005, and incorporated herein by reference. After the detection windows have been formed, the detection windows may be adjusted to account for gradual changes in the morphology of the cardiac signal. Methods and systems involving adjusting the size and/or timing of the detection windows to track gradual morphological changes are described in commonly owned U.S. patent application Ser. No. 11/116,578, filed Apr. 28, 2005, and incorporated herein by reference.

In some scenarios, arbitration processes in accordance with embodiments of the invention may be employed to determine the true peak amplitude and/or peak timing of the cardiac signal. Such processes may enhance the cardiac response classification when the cardiac signal peak occurs near the boundary between classification windows. For example, as illustrated in FIG. 3C, the peak 510 detected in a leading classification interval 420 may be a lesser or local event. In another example, illustrated in FIG. 3C, the peak value 511 measured at the boundary of a classification interval 420 is a transition point to the true peak 520 detected in the next classification interval 450.

As described above, it is possible that cardiac signal morphology is in transition at boundaries between classification intervals. Thus, it is possible that a peak measured in a leading window may be a lesser local event, or, if at a boundary, a transition point to a true peak in the next window. Methods and devices in accordance with embodiments of the present invention may perform arbitration of peaks or other cardiac signal features near the classification interval boundaries in order to provide true feature information to cardiac pacing response classification algorithms. An association may be established between portions of cardiac signals detected within adjacent classification intervals. The association may be established, for example, based on expected signal morphology. For purposes herein, the term adjacent classification windows includes windows with overlapping boundaries and separated boundaries, as well as windows that share a common boundary.

Figure 1C:
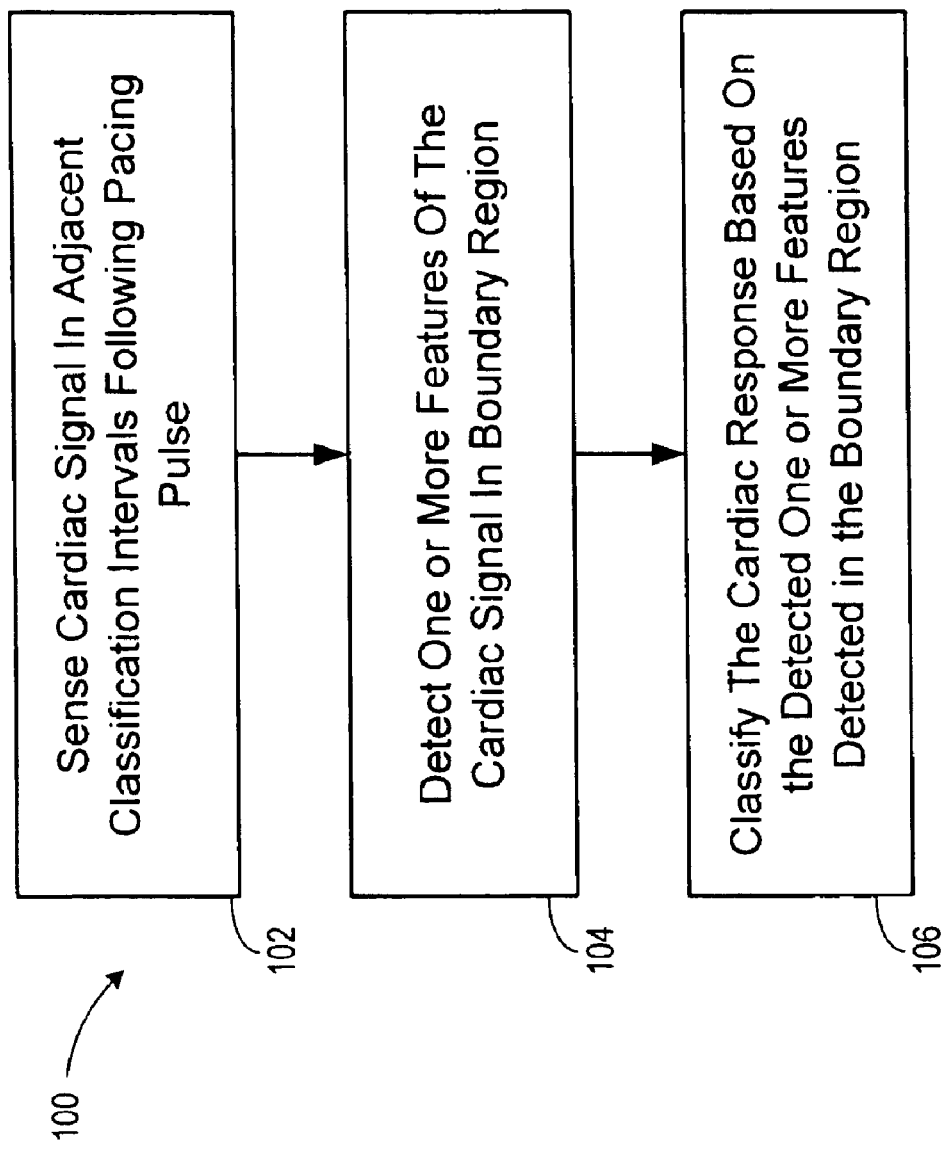
FIG. 1C is a flowchart of a method of classifying a cardiac response to a pacing pulse based on features in a boundary region of adjacent classification intervals in accordance with embodiments of the invention.

FIG. 1C is a flowchart of a method 100 of classifying a cardiac response to a pacing pulse based on features detected in adjacent classification intervals in accordance with embodiments of the invention. A cardiac signal is sensed 102 in adjacent classification intervals following a pacing pulse.

Cardiac signal features 104 are detected and, if determined to be within a boundary region of the adjacent classification intervals, are assessed for possible association with other features in the boundary region. The cardiac response to the pacing pulse may then be classified 106 based on the detected and associated cardiac signal features.

For example, the cardiac signal features used for pacing response classification may include features such as one or more of a peak amplitude, zero crossing, inflection point, and/or other features. In one implementation, measurement of the peak amplitude and peak time of the cardiac signal may be performed in each of two adjacent classification intervals. The time and amplitude values may be compared, and information generated from the comparison may be used to associate the measurements for more accurate peak amplitude and timing determination.

Cardiac signal features detected in a boundary region of the adjacent classification intervals may be assessed for association. The boundary region may be a region near a classification interval boundary, and/or may be defined as a predetermined arbitration interval, and/or may be defined relative to a classification window, and/or may be defined based on a relationship to one or more classification interval parameters. A boundary region may be established empirically, using patient data and/or clinical data, based on signal morphology and/or ranges of variation, for example.

An example of a measurement association that may be useful for the classification of a cardiac pacing response is to associate two maxima or minima. For example, a boundary region may straddle a common boundary of two adjacent classification intervals. A first peak (maxima or minima) may be measured in the first interval, and a second peak may be measured in the second interval. If both peaks are in the boundary region, and the magnitude of the first maxima is less than the magnitude of the second maxima, then the first maxima may be a local maxima and is associated with the second maxima, where the second maxima is determined to be the true cardiac signal peak.

Figure 2A:
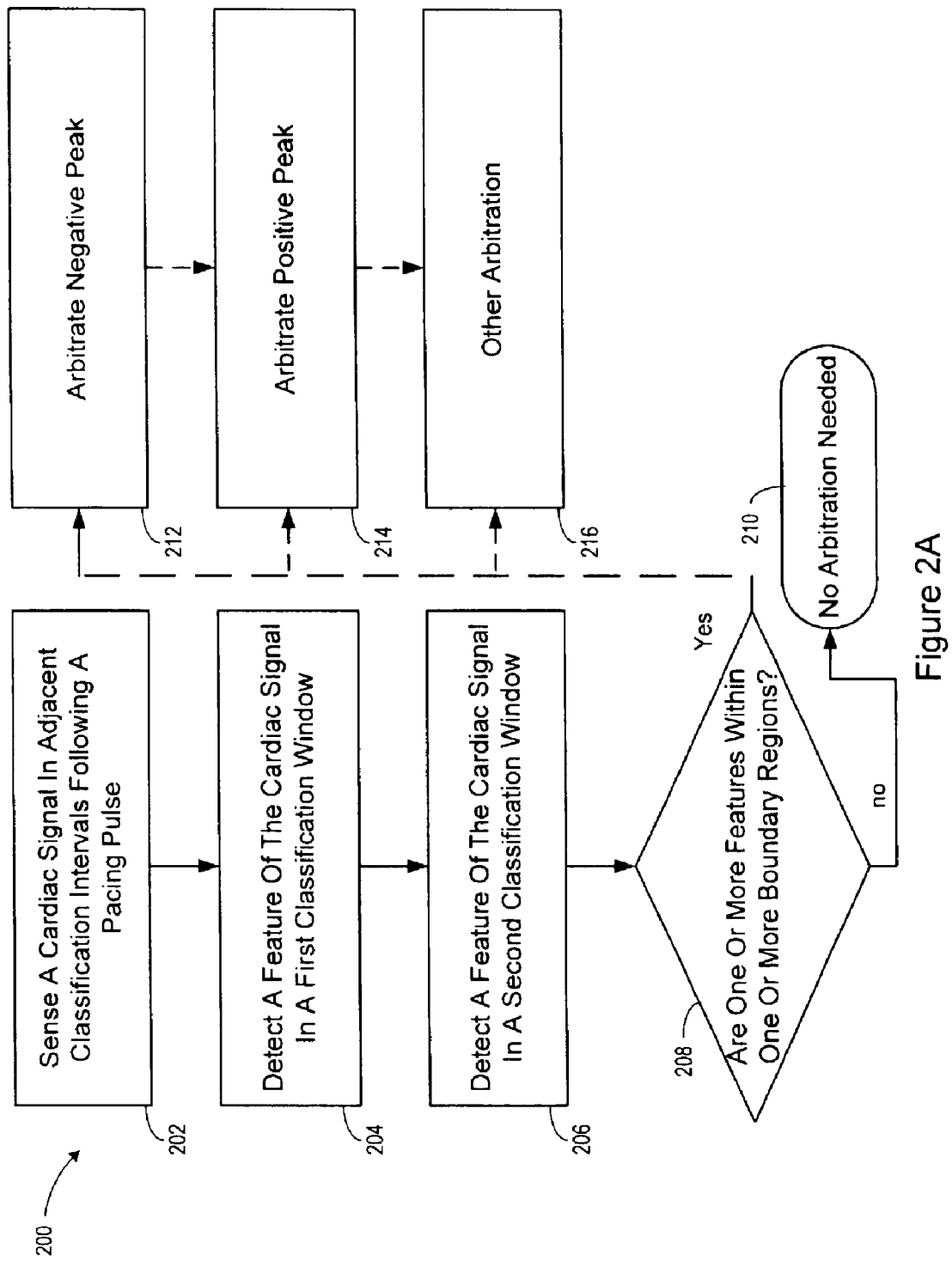
FIG. 2A is a flowchart of a method of detecting and associating signals between adjacent classification intervals in accordance with embodiments of the invention.

FIG. 2A is a flowchart of a method 200 of detecting and associating cardiac signal features across adjacent classification intervals in accordance with embodiments of the invention. A cardiac signal is sensed 202 over a time period encompassing at least two classification intervals, which are adjacent. Features, such as maximum and/or minimum value of the cardiac signal, may be detected 204 in one interval, detected 206 in a second interval, detected 204,206 in both intervals, and/or detected straddling the intervals (e.g. a peak at a common boundary between two intervals, or a peak in a space between two intervals that are adjacent, but separated).

A decision 208 is made as to whether one feature falls within a boundary region of a classification interval. If the decision 208 is no, then no arbitration of the feature(s) is needed 210. If the decision 208 is yes, then one or more arbitration events may occur to associate the features so that the associated features may be used for cardiac pacing response classification. For example, a negative peak arbitration 212, a positive peak arbitration 214, and/or other arbitration algorithms 216 may be performed to determine if features may be associated with other features and how the associated features should be used to best represent the cardiac signal for pacing response classification.

Figure 2B:
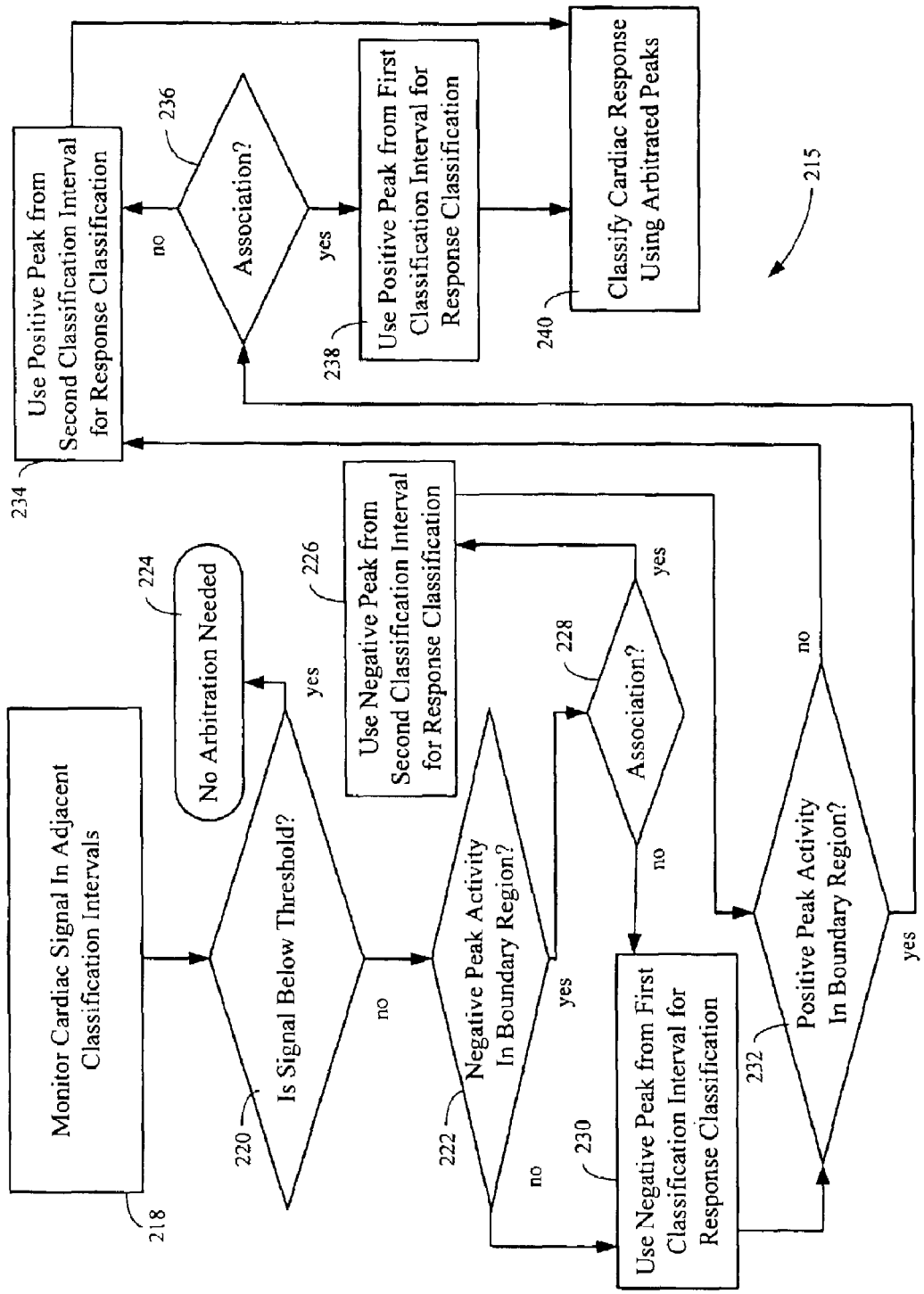
FIG. 2B is a flowchart of a method of arbitrating, between adjacent classification intervals, which interval to associate a cardiac signal feature with in accordance with embodiments of the invention.

FIG. 2B is a flowchart of a method 215 of arbitrating which cardiac signal features to use for cardiac pacing response classification in accordance with embodiments of the invention. A cardiac signal is monitored 218 after blanking in first and second adjacent classification intervals over a time period following a pacing pulse. If the positive or negative magnitude of the cardiac signal is below 220 a threshold, then no arbitration is needed 224, and loss of capture is indicated. If the positive or negative magnitude of the cardiac signal is beyond 220 the threshold, then loss of capture is not indicated, and the sensed signal may have features that would benefit from arbitration in accordance with embodiments of the invention.

The system measures signal features in first and second classification intervals. In this example, the system measures the following features in the first and second classification intervals: negative peak amplitude in the first classification interval, negative peak timing in the first classification interval, negative peak amplitude in the second classification interval, negative peak timing in the second classification interval, positive peak amplitude in the first classification interval, positive peak timing in the first classification interval, positive peak amplitude in the second classification interval, and positive peak timing in the second classification interval.

The system determines 222 if there is negative peak activity in a boundary region straddling the first and second classification intervals. If negative peaks of the cardiac signal sensed in the first and second classification intervals are within the boundary region, then arbitration is initiated. If there is no negative peak activity in the boundary region, the negative peak amplitude and timing of the first classification interval are used 230 in the cardiac response classification process.

The boundary region may comprise, for example, an interval of time that starts about 25 ms before the end of the first classification interval and continues until about 170 ms after the pacing pulse. The beginning of the boundary region may be selected, for example based on the timing of the first capture detection window 455, illustrated in FIG. 1B. The beginning of the boundary region may be selected to cover small signal variations that may occur at the end of the first classification interval. The end of the boundary region may be selected based on empirical data extremes of negative peaks for cardiac signals representing normal captured responses and noncapture responses with intrinsic activation.

The arbitration process involves determining if an association exists 228 between a negative peak occurring in the first classification interval and a negative peak occurring in the second classification interval. For example, the actual peak of the cardiac signal may occur in the second classification interval with the cardiac signal in the first classification interval decreasing toward the negative peak at the end of the first classification interval, as illustrated in FIG. 3C. In this scenario, the most negative value of the cardiac signal in the first classification interval may represent an apparent peak of the cardiac signal and the most negative value in the second classification interval may represent an actual peak of the cardiac signal. The two negative values are associated by the expected morphology of the cardiac response. The process of determining the association between the negative peaks in the first and second classification intervals and how to best use the association to represent the cardiac response, reduces the likelihood that intrinsic and/or PVC activity will be erroneously relied upon as an indication of capture or fusion, and that capture responses are properly represented in the peak features of the cardiac signal regardless of classification interval boundaries.

The association between the negative peaks in the first and second classification intervals may be determined 228 based on the expected morphology of the cardiac signal. For example, for a captured response or a fusion beat, the expected cardiac signal morphology is that a negative peak occurs before a positive peak. In one implementation, if the timing of the negative peak in the second classification interval occurs before the positive peak timing in the second classification interval, and the negative peak amplitude in the first classification interval is less than the negative peak amplitude in the second classification interval, then the negative peak in the first classification interval is associated 228 with the negative peak in the second classification interval and the system uses 226 the negative peak amplitude and timing from the second classification interval for cardiac response classification.

If the timing of the negative peak in the second classification interval occurs after the positive peak timing in the second classification interval, or if the negative peak amplitude in the first classification interval is greater than the negative peak amplitude in the second classification interval, then the negative peak occurring in the first classification interval is not associated 228 with the negative peak occurring in the second classification interval and the system uses 230 the negative peak amplitude and timing from the first classification interval in the cardiac response classification process.

The system determines 232 if there is positive peak activity in the boundary region straddling the first and second classification intervals. The boundary region used for the negative peak arbitration may be different from or the same as the boundary region used for the positive peak arbitration. If either first or second classification interval positive peaks are not in the boundary region 232, the positive peak amplitude and timing from the second classification interval are used 234 for cardiac response classification. If the timing of the positive peaks in the first and second classification intervals are within 232 the boundary region, then the arbitration process may be initiated.

The arbitration process involves determining if an association exists 236 between a positive peak occurring in the first classification interval and a positive peak occurring in the second classification interval. For example, an association may exist 236 when the positive peak of the first classification interval represents an actual peak and the positive peak detected in the second classification interval represents an apparent peak. Thus, the actual positive peak of the cardiac signal may occur in the first classification interval with the cardiac signal in the second classification interval decreasing after the peak. The arbitration process determines whether to use the peak occurring in the first classification interval or the peak occurring in the second classification interval for cardiac pacing response classification.

The association between the positive peak in the first classification interval and the positive peak in the second classification interval may be determined 236 based on the expected morphology of the cardiac signal. For example, for a captured response or a fusion beat, the expected cardiac signal morphology is that a negative peak occurs before a positive peak. Thus, positive peak arbitration is indicated if the arbitrated negative peak occurs before the positive peak. In one implementation, if the positive peak amplitude of the first classification interval is greater than the positive peak amplitude of the second classification interval, then the positive peak in the first classification interval is associated 236 with the positive peak in the second classification interval and the system uses 238 the positive peak amplitude and timing from the first classification interval for cardiac response classification.

If the positive peak amplitude of the first classification interval is less than the positive peak amplitude of the second classification interval, then the positive peak occurring in the first classification interval is not associated 236 with the positive peak occurring in the second classification interval and the system uses 234 the positive peak amplitude and timing from the second classification interval as the positive peak features in the cardiac response classification process.

After associating the signal features using the processes as illustrated in FIG. 2B, the cardiac signal may now be classified 240. The arbitration process of the present invention provides less chance of a signal transition between interval boundaries that may affect cardiac pacing response discrimination.

Figure 3A:
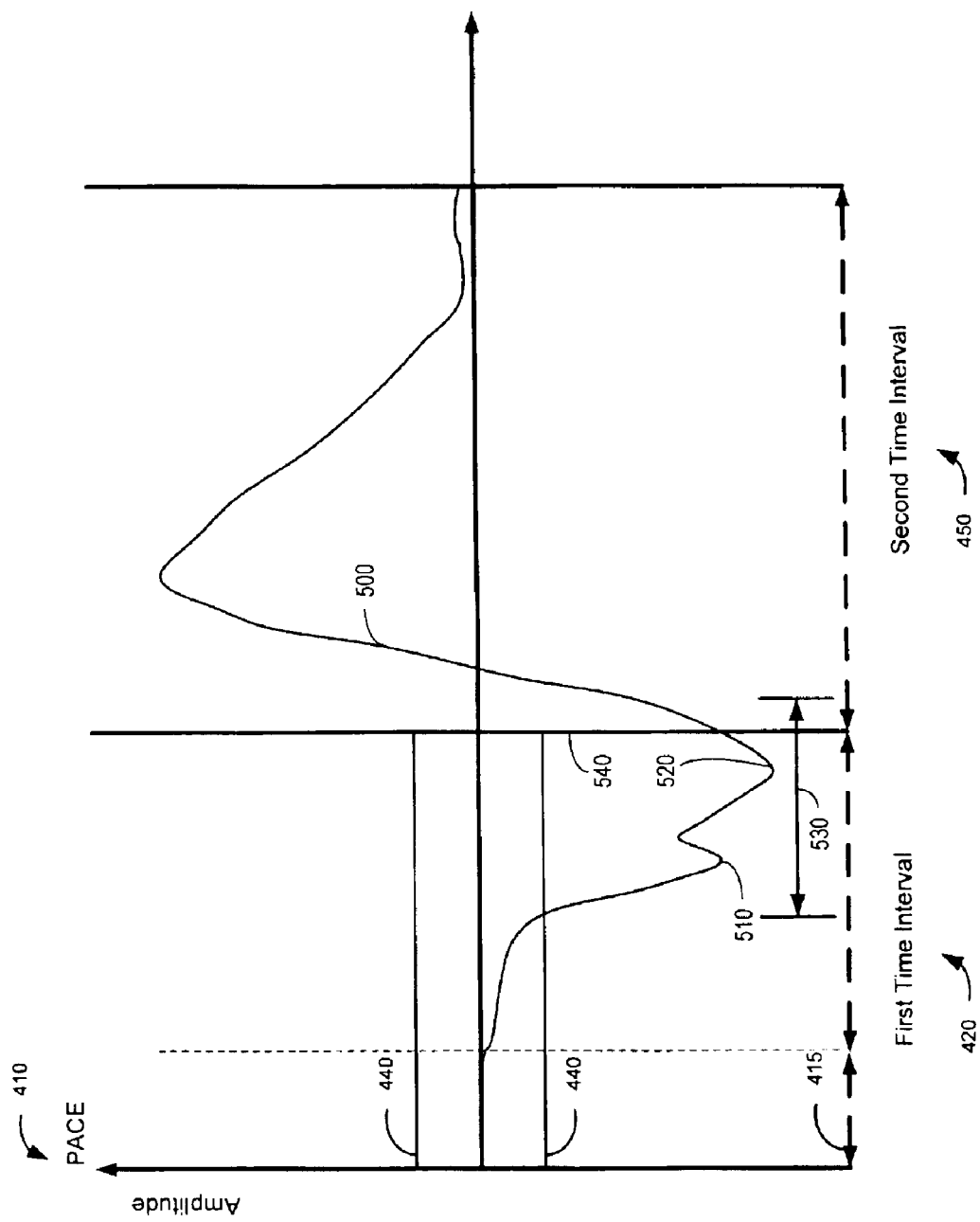
FIGS. 3A, 3B and 3C illustrate cardiac response waveform portions superimposed over the classification intervals of FIG. 1 in accordance with embodiments of the invention.
Figure 3B:
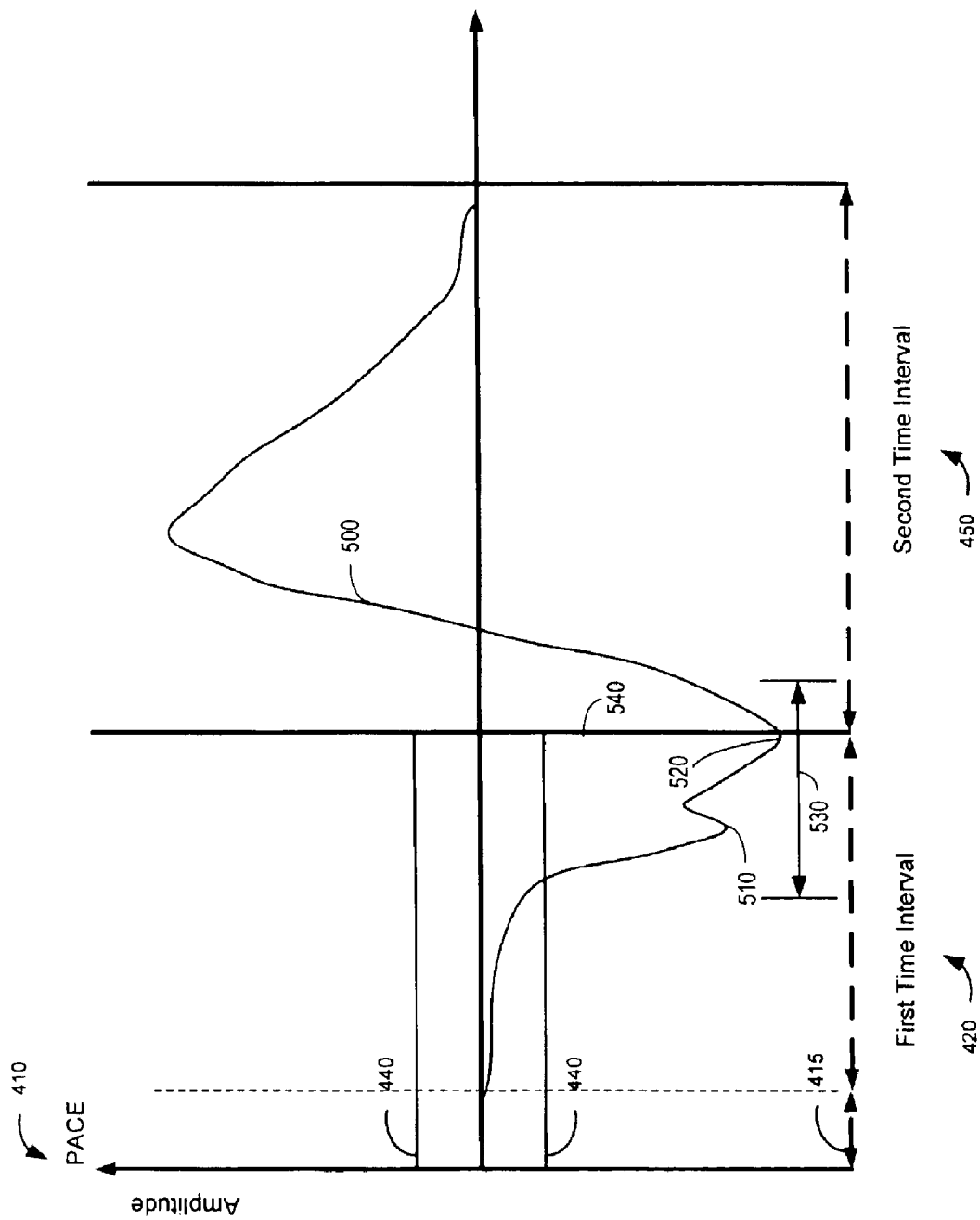
Figure 3C:
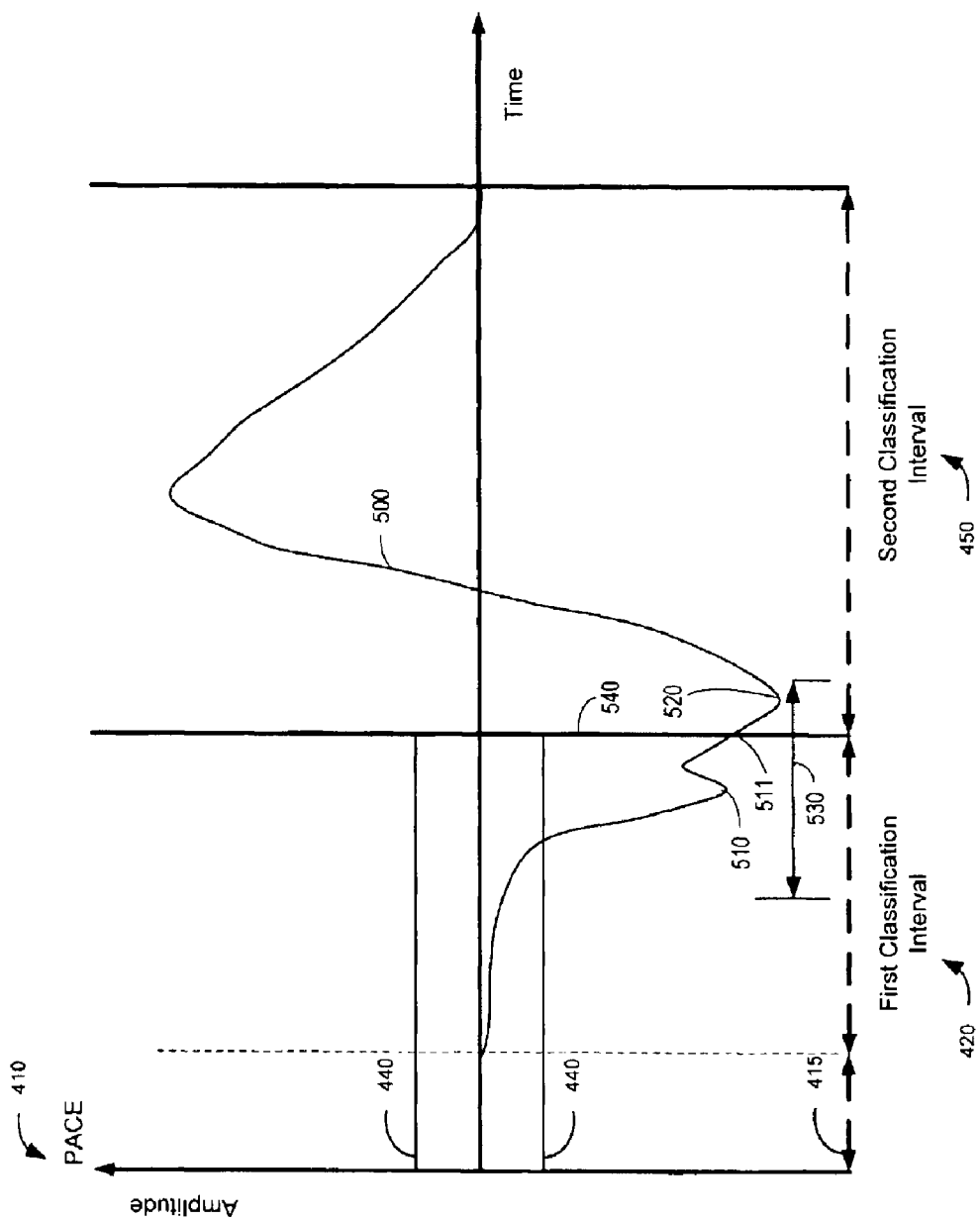

FIGS. 3A, 3B and 3C illustrate a representative sensed cardiac signal 500 superimposed over the graph illustrated in FIG. 1A. The sensed cardiac signal 500 includes a first minimum peak 510 and a second minimum peak 520. A boundary region 530 is designated about a boundary 540 between the first time interval 420 and the second time interval 450. In the graph of FIG. 3A, the minimum value in the first time interval 420 is the minimum peak 520, and the minimum value in the second time interval 450 occurs where the signal 500 intersects the boundary 540. Both minimum values are in the boundary region 530 and arbitration is needed in accordance with embodiments of the invention. Referring to the process illustrated in FIG. 2B, the two minimum values would not be associated and the second minimum value 520 in the first time interval 420 would be used to classify the cardiac response. This condition would typically not cause an erroneous peak detection.

In the graph of FIG. 3B, the first minimum peak 510 is in the first time interval 420 and the second minimum peak 520 straddles the boundary 540. This situation may benefit from arbitration in accordance with the present invention. Arbitration may be used to increase the likelihood that the minimum peak 520 is used for classifying the cardiac response regardless of the time interval 420, 450 the minimum peak 520 actually resides in.

In the graph of FIG. 3C, the first minimum peak 510 is in the first time interval 420 and the second minimum peak 520 is in the second time interval 450. This situation would produce an erroneous result of the first minimum peak 510 being accepted as the true minimum peak unless arbitration in accordance with the present invention were used to associate the local minimum peak 510 with the true minimum peak 520.

The embodiments of the present system illustrated herein are generally described as being implemented in a cardiac rhythm management system such as an implantable cardiac defibrillator/pacemaker that may operate in numerous pacing modes known in the art. Various types of single and multiple chamber implantable cardiac defibrillators are known in the art and may be used in connection with cardiac devices and methods that detect one or more features of cardiac signals near boundaries of adjacent classification intervals, determining feature associations and classifying the cardiac response based on the features and their associations, in accordance with the present invention. The methods of the present invention may also be implemented in a variety of implantable or patient-external cardiac rhythm management devices, including single and multi-chamber pacemakers, defibrillators, cardioverters, bi-ventricular pacemakers, cardiac resynchronizers, and cardiac monitoring systems, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 4:
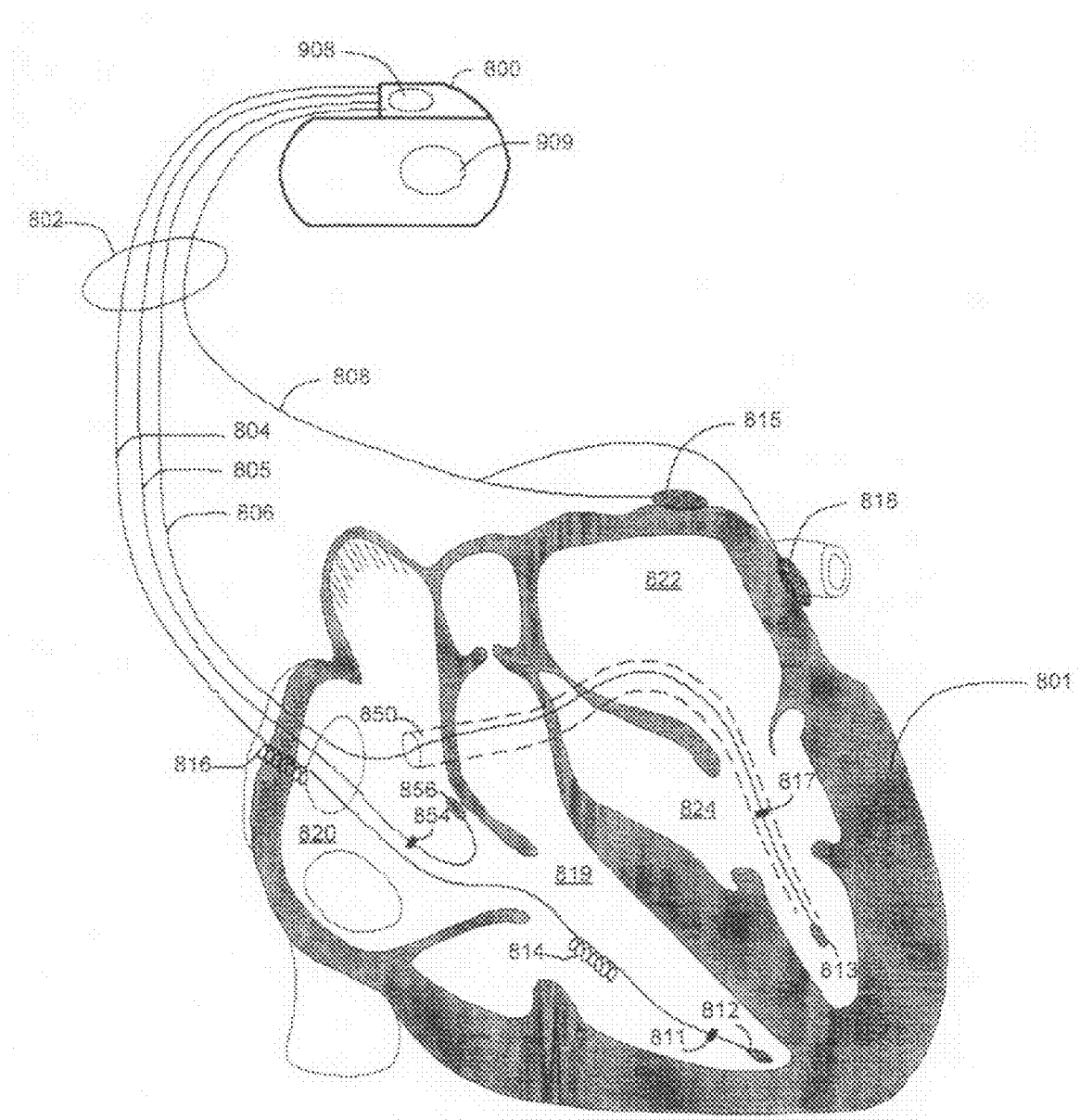
FIG. 4 is a partial view of one embodiment of an implantable medical device in accordance with embodiments of the invention.

Referring now to FIG. 4 of the drawings, there is shown a cardiac rhythm management system that may be used to implement adjacent classification interval feature detection, boundary feature association and arbitration, and resulting cardiac response classification methods in accordance with the present invention. The cardiac rhythm management system in FIG. 4 includes a pacemaker/defibrillator 800 electrically and physically coupled to a lead system 802. The housing and/or header of the pacemaker/defibrillator 800 may incorporate one or more electrodes 908, 909 used to provide electrical stimulation energy to the heart and to sense cardiac electrical activity. The pacemaker/defibrillator 800 may utilize all or a portion of the pacemaker/defibrillator housing as a can electrode 909. The pacemaker/defibrillator 800 may include an indifferent electrode 908 positioned, for example, on the header or the housing of the pacemaker/defibrillator 800. If the pacemaker/defibrillator 800 includes both a can electrode 909 and an indifferent electrode 908, the electrodes 908, 909 typically are electrically isolated from each other.

The lead system 802 is used to detect electric cardiac signals produced by the heart 801 and to provide electrical energy to the heart 801 under certain predetermined conditions to treat cardiac arrhythmias. The lead system 802 may include one or more electrodes used for pacing, sensing, and/or defibrillation. In the embodiment shown in FIG. 4, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 4 illustrates one embodiment that may be used in connection with the feature association and determination methodologies described herein. Other leads and/or electrodes may additionally or alternatively be used.

The lead system 802 may include intracardiac leads 804, 805, 806 implanted in a human body with portions of the intracardiac leads 804, 805, 806 inserted into a heart 801. The intracardiac leads 804, 805, 806 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 4, the lead system 802 may include one or more extracardiac leads 808 having electrodes, e.g., epicardial electrodes, positioned at locations outside the heart for sensing and pacing one or more heart chambers.

The right ventricular lead system 804 illustrated in FIG. 4 includes an SVC-coil 816, an RV-coil 814, an RV-ring electrode 811, and an RV-tip electrode 812. The right ventricular lead system 804 extends through the right atrium 820 and into the right ventricle 819. In particular, the RV-tip electrode 812, RV-ring electrode 811, and RV-coil electrode 814 are positioned at appropriate locations within the right ventricle 819 for sensing and delivering electrical stimulation pulses to the heart 801. The SVC-coil 816 is positioned at an appropriate location within the right atrium chamber 820 of the heart 801 or a major vein leading to the right atrial chamber 820 of the heart 801.

In one configuration, the RV-tip electrode 812 referenced to the can electrode 909 may be used to implement unipolar pacing and/or sensing in the right ventricle 819. Bipolar pacing and/or sensing in the right ventricle may be implemented using the RV-tip 812 and RV-ring 811 electrodes. In yet another configuration, the RV-ring 811 electrode may optionally be omitted, and bipolar pacing and/or sensing may be accomplished using the RV-tip electrode 812 and the RV-coil 814, for example. The RV-coil 814 and the SVC-coil 816 are defibrillation electrodes.

The left ventricular lead 806 includes an LV distal electrode 813 and an LV proximal electrode 817 located at appropriate locations in or about the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824 which are not directly accessible from the right side of the heart. Lead placement for the left ventricular lead 806 may be achieved via subclavian vein access and a preformed guiding catheter for insertion of the LV electrodes 813, 817 adjacent to the left ventricle.

Unipolar pacing and/or sensing in the left ventricle may be implemented, for example, using the LV distal electrode referenced to the can electrode 909. The LV distal electrode 813 and the LV proximal electrode 817 may be used together as bipolar sense and/or pace electrodes for the left ventricle. The left ventricular lead 806 and the right ventricular lead 804, in conjunction with the pacemaker/defibrillator 800, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 805 includes a RA-tip electrode 856 and an RA-ring electrode 854 positioned at appropriate locations in the right atrium 820 for sensing and pacing the right atrium 820. In one configuration, the RA-tip 856 referenced to the can electrode 909, for example, may be used to provide unipolar pacing and/or sensing in the right atrium 820. In another configuration, the RA-tip electrode 856 and the RA-ring electrode 854 may be used to provide bipolar pacing and/or sensing.

FIG. 4 illustrates one embodiment of a left atrial lead system 808. In this example, the left atrial lead 808 is implemented as an extracardiac lead with LA distal 818 and LA proximal 815 electrodes positioned at appropriate locations outside the heart 801 for sensing and pacing the left atrium 822. Unipolar pacing and/or sensing of the left atrium may be accomplished, for example, using the LA distal electrode 818 to the can 909 pacing vector. The LA proximal 815 and LA distal 818 electrodes may be used together to implement bipolar pacing and/or sensing of the left atrium 822.

Figure 5:
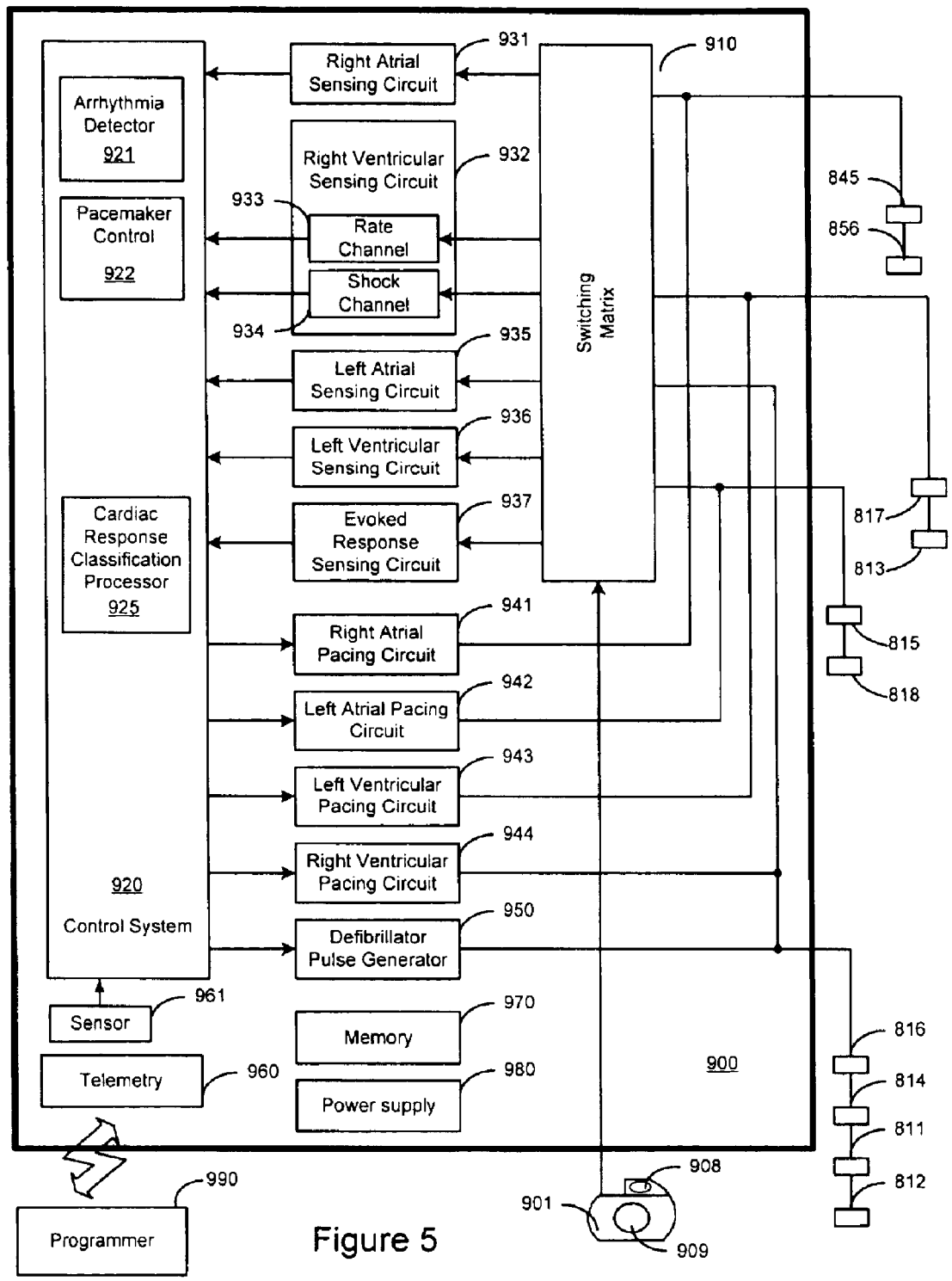
FIG. 5 is a block diagram of an implantable medical device that may classify a cardiac response to a pacing pulse in accordance with embodiments of the invention.

Referring now to FIG. 5, there is shown an embodiment of a cardiac pacemaker/defibrillator 900 suitable for implementing feature association and capture detection methods of the present invention. FIG. 5 shows a cardiac pacemaker/defibrillator 900 divided into functional blocks. It is understood by those skilled in the art that there exist many possible configurations in which these functional blocks can be arranged. The example depicted in FIG. 5 is one possible functional arrangement. Other arrangements are also possible. For example, more, fewer or different functional blocks may be used to describe a cardiac pacemaker/defibrillator suitable for implementing the methodologies for feature association and determination in accordance with the present invention. In addition, although the cardiac pacemaker/defibrillator 900 depicted in FIG. 5 contemplates the use of a programmable microprocessor-based logic circuit, other circuit implementations may be utilized.

The cardiac pacemaker/defibrillator 900 depicted in FIG. 5 includes circuitry for receiving cardiac signals from a heart and delivering electrical stimulation energy to the heart in the form of pacing pulses or defibrillation shocks. In one embodiment, the circuitry of the cardiac pacemaker/defibrillator 900 is encased and hermetically sealed in a housing 901 suitable for implanting in a human body. Power to the cardiac pacemaker/defibrillator 900 is supplied by an electrochemical battery 980. A connector block (not shown) is attached to the housing 901 of the cardiac pacemaker/defibrillator 900 to allow for the physical and electrical attachment of the lead system conductors to the circuitry of the cardiac pacemaker/defibrillator 900.

The cardiac pacemaker/defibrillator 900 may be a programmable microprocessor-based system, including a control system 920 and a memory 970. The memory 970 may store parameters for various pacing, defibrillation, and sensing modes, along with other parameters. Further, the memory 970 may store data indicative of cardiac signals received by other components of the cardiac pacemaker/defibrillator 900. The memory 970 may be used, for example, for storing historical EGM and therapy data. The historical data storage may include, for example, data obtained from long-term patient monitoring used for trending and/or other diagnostic purposes. Historical data, as well as other information, may be transmitted to an external programmer unit 990 as needed or desired.

The control system 920 and memory 970 may cooperate with other components of the cardiac pacemaker/defibrillator 900 to control the operations of the cardiac pacemaker/defibrillator 900. The control system depicted in FIG. 5 incorporates a cardiac response classification processor 925 for classifying cardiac responses to pacing stimulation. The cardiac response classification processor performs the function of arbitrating and associating cardiac signal features for pacing response classification in accordance with embodiments of the invention. The control system 920 may include additional functional components including a pacemaker control circuit 922, an arrhythmia detector 921, along with other components for controlling the operations of the cardiac pacemaker/defibrillator 900.

Telemetry circuitry 960 may be implemented to provide communications between the cardiac pacemaker/defibrillator 900 and an external programmer unit 990. In one embodiment, the telemetry circuitry 960 and the programmer unit 990 communicate using a wire loop antenna and a radio frequency telemetric link, as is known in the art, to receive and transmit signals and data between the programmer unit 990 and the telemetry circuitry 960. In this manner, programming commands and other information may be transferred to the control system 920 of the cardiac pacemaker/defibrillator 900 from the programmer unit 990 during and after implant. In addition, stored cardiac data pertaining to capture threshold, capture detection and/or cardiac response classification, for example, along with other data, may be transferred to the programmer unit 990 from the cardiac pacemaker/defibrillator 900.

The telemetry circuitry 960 may provide for communication between the cardiac pacemaker/defibrillator 900 and an advanced patient management (APM) system. The advanced patient management system allows physicians or other personnel to remotely and automatically monitor cardiac and/or other patient conditions. In one example, a cardiac pacemaker/defibrillator, or other device, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

In the embodiment of the cardiac pacemaker/defibrillator 900 illustrated in FIG. 5, electrodes RA-tip 856, RA-ring 854, RV-tip 812, RV-ring 811, RV-coil 814, SVC-coil 816, LV distal electrode 813, LV proximal electrode 817, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 856 and the RA-ring 854. Unipolar sensing may be implemented, for example, by sensing voltages developed between the RA-tip 856 and the can electrode 909. Outputs from the right atrial sensing circuit are coupled to the control system 920.

A right ventricular sensing circuit 932 serves to detect and amplify electrical signals from the right ventricle of the heart. The right ventricular sensing circuit 932 may include, for example, a right ventricular rate channel 933 and a right ventricular shock channel 934. Right ventricular cardiac signals sensed through use of the RV-tip 812 electrode are right ventricular near-field signals and are denoted RV rate channel signals. A bipolar RV rate channel signal may be sensed as a voltage developed between the RV-tip 812 and the RV-ring 811. Alternatively, bipolar sensing in the right ventricle may be implemented using the RV-tip electrode 812 and the RV-coil 814. Unipolar rate channel sensing in the right ventricle may be implemented, for example, by sensing voltages developed between the RV-tip 812 and the can electrode 909.

Right ventricular cardiac signals sensed through use of the defibrillation electrodes are far-field signals, also referred to as RV morphology or RV shock channel signals. More particularly, a right ventricular shock channel signal may be detected as a voltage developed between the RV-coil 814 and the SVC-coil 816. A right ventricular shock channel signal may also be detected as a voltage developed between the RV-coil 814 and the can electrode 909. In another configuration the can electrode 909 and the SVC-coil electrode 816 may be electrically shorted and a RV shock channel signal may be detected as the voltage developed between the RV-coil 814 and the can electrode 909/SVC-coil 816 combination.

Outputs from the right ventricular sensing circuit 932 are coupled to the control system 920. In one embodiment of the invention, rate channel signals and shock channel signals may be used to develop morphology templates for analyzing cardiac signals. In this embodiment, rate channel signals and shock channel signals may be transferred from the right ventricular sensing circuit 932 to the control system 920 and analyzed for arrhythmia detection.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to can vector 909 or the LA proximal electrode 815 to can vector 909.

A left ventricular sensing circuit 936 serves to detect and amplify electrical signals from the left ventricle of the heart. Bipolar sensing in the left ventricle may be implemented, for example, by sensing voltages developed between the LV distal electrode 813 and the LV proximal electrode 817. Unipolar sensing may be implemented, for example, by sensing voltages developed between the LV distal electrode 813 or the LV proximal electrode 817 and the can electrode 909.

Optionally, an LV coil electrode (not shown) may be inserted into the patient's cardiac vasculature, e.g., the coronary sinus, adjacent the left heart. Signals detected using combinations of the LV electrodes, 813, 817, LV coil electrode (not shown), and/or can electrodes 909 may be sensed and amplified by the left ventricular sensing circuitry 936. The output of the left ventricular sensing circuit 936 is coupled to the control system 920.

The outputs of the switching matrix 910 may be operated to couple selected combinations of electrodes 811, 812, 813, 814, 815, 816, 817, 818, 856, 854 to an evoked response sensing circuit 937. The evoked response sensing circuit 937 serves to sense and amplify voltages developed using various combinations of electrodes for discrimination of various cardiac responses to pacing in accordance with embodiments of the invention. The cardiac response classification processor 925 may analyze the output of the evoked response sensing circuit 937 to implement feature association and cardiac pacing response classification in accordance with embodiments of the invention.

Various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing. In other embodiments, the same electrode combination is used for pacing and sensing. Use of different electrodes for pacing and sensing in connection with capture verification is described in commonly owned U.S. Pat. No. 6,128,535 which is incorporated herein by reference.

The pacemaker control circuit 922, in combination with pacing circuitry for the left atrium, right atrium, left ventricle, and right ventricle 941, 942, 943, 944, may be implemented to selectively generate and deliver pacing pulses to the heart using various electrode combinations. The pacing electrode combinations may be used to effect bipolar or unipolar pacing pulses to a heart chamber using one of the pacing vectors as described above. In some implementations, the cardiac pacemaker/defibrillator 900 may include a sensor 961 that is used to sense the patient's hemodynamic need. The pacing output of the cardiac pacemaker/defibrillator may be adjusted based on the sensor 961 output.

The electrical signal following the delivery of the pacing pulses may be sensed through various sensing vectors coupled through the switch matrix 910 to the evoked response sensing circuit 937 and used to classify the cardiac response to pacing. The cardiac response may be classified as one of a captured response, a non-captured response, a non-captured response with intrinsic activation, and a fusion/pseudofusion beat, for example.

Subcutaneous electrodes may provide additional sensing vectors useable for cardiac response classification. In one implementation, cardiac rhythm management system may involve a hybrid system including an intracardiac device configured to pace the heart and an extracardiac device, e.g., a subcutaneous defibrillator, configured to perform functions other than pacing. The extracardiac device may be employed to detect and classify cardiac response to pacing based on signals sensed using subcutaneous electrode arrays. The extracardiac and intracardiac devices may operate cooperatively with communication between the devices occurring over a wireless link, for example. Examples of subcutaneous electrode systems and devices are described in commonly owned U.S. patent application Ser. Nos. 10/462,001, filed Jun. 13, 2003 and 10/465,520, filed Jun. 19, 2003, which are hereby incorporated herein by reference in their respective entireties.

Figure 6:
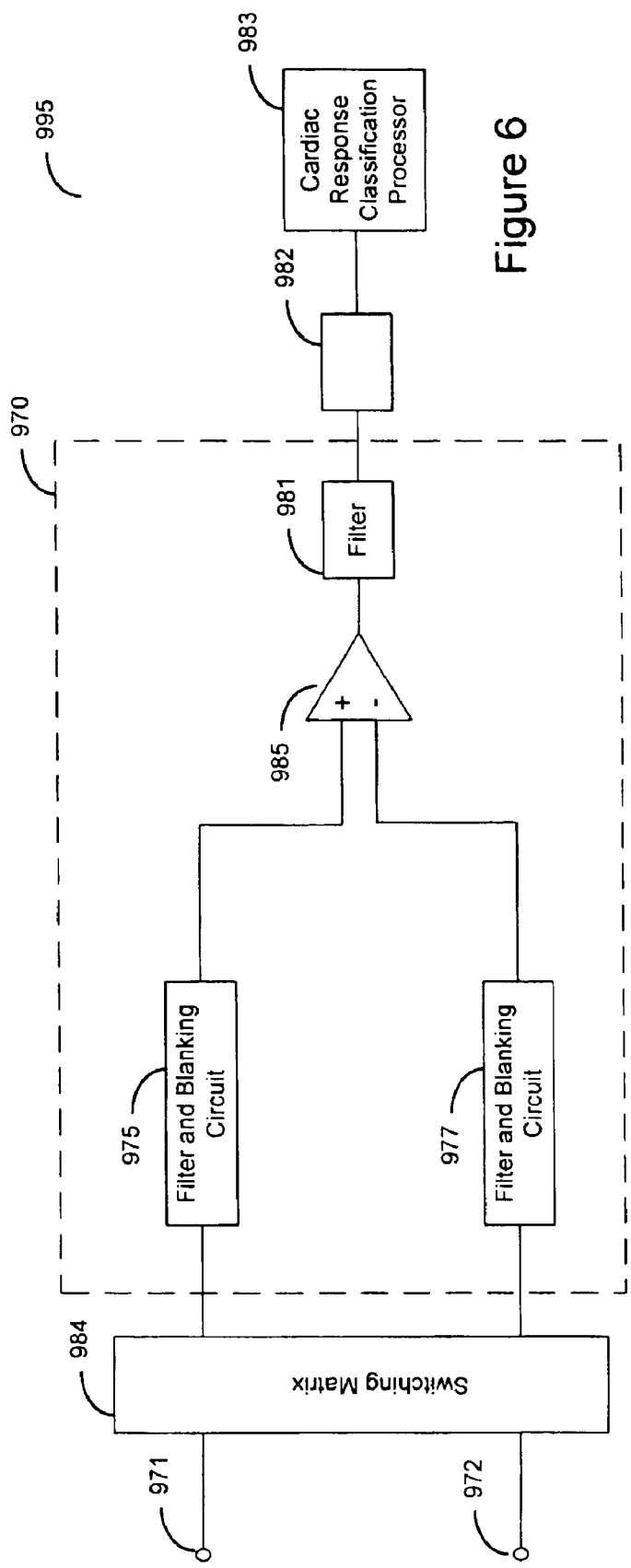
FIG. 6 is a schematic diagram of a circuit that may be used to sense a cardiac signal following the delivery of a pacing stimulation and to classify the cardiac response to the pacing stimulation according to embodiments of the invention.

FIG. 6 illustrates a block diagram of circuit 995 that may be used to sense cardiac signals following the delivery of a pacing stimulation and classify the cardiac response to the pacing stimulation according to embodiments of the invention. A switch matrix 984 is used to couple the cardiac electrodes 971, 972 in various combinations discussed above to the sensing portion 970 of the cardiac response classification circuit 995. The sensing portion 970 includes filtering and blanking circuitry 975, 977, sense amplifier 985, band pass filter 981, and window generation and signal characteristic detector 982. The window generation and signal characteristic detector 982 is coupled to a cardiac response classification processor 983.

A control system, e.g., the control system 920 depicted in FIG. 5, is operatively coupled to components of the cardiac sensing circuit 995 and controls the operation of the circuit 995, including the filtering and blanking circuits 975, 977. Following delivery of the pacing stimulation, the blanking circuitry 975, 977 operates for a sufficient duration and then allows detection of a cardiac signal responsive to the pacing stimulation. The cardiac signal is filtered, amplified, and converted from analog to digital form. The digitized signal is communicated to the cardiac response classification processor 983, which operates in cooperation with other components of the control system 920 (FIG. 5) to classify cardiac responses to pacing according to embodiments of the invention.

Various modifications and additions can be made to the embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of operating a cardiac rhythm management device for classifying a cardiac response to a pacing pulse, comprising:

timing a plurality of cardiac pacing response classification intervals following delivery of the pacing pulse;

sensing a cardiac signal in at least two classification intervals of the plurality of classification intervals;

detecting at least one cardiac signal feature that occurs within a boundary region, the boundary region at least partially overlapping the at least two classification intervals;

classifying the cardiac response to the pacing pulse based on the detected cardiac signal feature; and delivering pacing therapy based at least in part on classification of the cardiac response to the pacing pulse.

2. The method of claim 1, wherein the at least two classification intervals have a common boundary.

3. The method of claim 1, wherein the at least two classification intervals are separated by a time interval.

4. The method of claim 1, wherein classifying the cardiac response to the pacing pulse comprises:

associating portions of the at least one cardiac signal feature that occur within the boundary region; and classifying the cardiac response to the pacing pulse based on the associated portions.

5. The method of claim 4, wherein associating the portions of the cardiac signal feature comprises associating the portions based on expected signal morphology.

6. The method of claim 5, wherein the expected signal morphology includes an expectation that a negative peak occurs before a positive peak.

7. The method of claim 4, wherein associating the portions of the cardiac signal feature comprises associating based on an expected time of the cardiac signal feature.

8. The method of claim 1, wherein the cardiac signal feature comprises a signal peak.

9. The method of claim 1, wherein the at least one cardiac signal feature comprises one or both of a positive cardiac signal peak and a negative cardiac signal peak.

10. The method of claim 1, wherein:
detecting the at least one cardiac signal feature in the boundary region comprises:
    detecting a first portion of a cardiac signal peak in a first classification interval;
    detecting a second portion of the cardiac signal peak in a second classification interval; and
    associating the first and the second portions of the cardiac signal peak; and
classifying the cardiac response to the pacing pulse comprises classifying the cardiac response to the pacing pulse based on the associated portions of the cardiac signal peak.

11. A system for characterizing a cardiac response to pacing, comprising:
a sensing system configured to sense cardiac signals following pacing pulses delivered to a heart;
a processor coupled to the sensing system, the processor configured to time a plurality of classification intervals following delivery of a pacing pulse, detect a cardiac signal feature that occurs within a boundary region, the boundary region at least partially overlapping at least two classification intervals of the plurality of classification intervals, and classify the cardiac response to the pacing pulse based on the cardiac signal feature; and
a pacing circuit configured to deliver pacing therapy based at least in part on classification of the cardiac pacing response.

12. The system of claim 11, wherein the processor is configured to associate portions of the cardiac signal feature detected within the boundary region.

13. The system of claim 12, wherein the portions of the cardiac signal feature comprise portions of a negative signal peak or portions of a positive signal peak.

14. The system of claim 11, wherein the processor is configured to evaluate the cardiac signal feature across the plurality of classification intervals to determine feature information associated with the cardiac signal feature.

15. The system of claim 11, wherein the processor is configured to associate portions of the cardiac signal feature that occur within the two classification intervals if timing of the portions satisfies an expected signal morphology.

16. The system of claim 11, wherein the at least two classification intervals have a common temporal border.

17. The system of claim 11, wherein the at least two classification intervals are temporally non-continuous.

18. A system for characterizing a cardiac response to pacing, comprising:
means for sensing a cardiac signal in at least two classification intervals;
means for classifying a cardiac response to a pacing pulse, including means for detecting at least one cardiac signal feature that occurs within a boundary region that at least partially overlaps the at least two classification intervals and means for classifying the cardiac response to the pacing pulse based on the detected cardiac signal feature; and
circuitry configured to deliver pacing therapy based at least in part on classification of the cardiac response to the pacing pulse.

19. The system of claim 18, wherein the means for classifying associates portions of one or more cardiac signal peaks that fall within the boundary region based on expected signal morphology.

20. The system of claim 18, wherein the at least one cardiac signal feature comprises one or more cardiac signal peaks.

* * * * *